US011176802B1

(12) United States Patent
Robinson

(10) Patent No.: US 11,176,802 B1
(45) Date of Patent: Nov. 16, 2021

(54) WEARABLE HEALTH AND TREATMENT DEVICE

(71) Applicants: Ernest Radford Robinson, Lithonia, GA (US); Muhammad Robinson, La Quinta, CA (US)

(72) Inventor: Ernest Radford Robinson, Lithonia, GA (US)

(73) Assignees: Ernest Radford Robinson, Lithonia, GA (US); Muhammad Robinson, La Quinta, CA (US)

( * ) Notice: Subject to any disclaimer, the term of this patent is extended or adjusted under 35 U.S.C. 154(b) by 0 days.

(21) Appl. No.: 16/912,192

(22) Filed: Jun. 25, 2020

(51) Int. Cl.

*G08B 21/24* (2006.01)
*A61B 5/00* (2006.01)
*G06F 1/16* (2006.01)
*A47K 5/12* (2006.01)

(52) U.S. Cl.

CPC .......... *G08B 21/245* (2013.01); *A47K 5/1201* (2013.01); *A61B 5/0008* (2013.01); *A61B 5/681* (2013.01); *A61B 5/742* (2013.01); *G06F 1/163* (2013.01)

(58) Field of Classification Search

CPC .. G08B 21/245; A47K 5/1201; A61B 5/0008; A61B 5/681; A61B 5/742; G06F 1/163

See application file for complete search history.

(56) References Cited

U.S. PATENT DOCUMENTS 4,407,295 A * 10/1983 Steuer ................ A61B 5/02438 600/483
5,050,612 A * 9/1991 Matsumura ........ A61B 5/14532 600/483
5,217,143 A 6/1993 Aitken
5,316,182 A 5/1994 Lee et al.
5,358,144 A 10/1994 Mock
5,752,512 A * 5/1998 Gozani .................... A61B 5/05 600/347
5,927,548 A 7/1999 Villaveces
6,269,265 B1 * 7/2001 Anderson ............... A61N 1/30 604/20
6,506,183 B2 1/2003 Cogger
6,814,265 B2 11/2004 Clifford et al.
7,316,332 B2 * 1/2008 Powers ................. A45D 34/00 222/1

(Continued)

*Primary Examiner* — Joseph H Feild
*Assistant Examiner* — Rufus C Point
(74) *Attorney, Agent, or Firm* — Alston & Bird LLP

(57) ABSTRACT

A wearable device and systems and methods including the wearable device are provided. The wearable device includes a wearable strap, the wearable strap having a first cavity extending along a portion of the wearable strap; a deformable cartridge positioned substantially within the first cavity and configured to contain and selectively dispense a treatment substance; a body temperature capturing component, one side of the body temperature capturing component being in contact with a portion of a wearer's skin, and an opposing side of the body temperature capturing component being in contact with the deformable cartridge; and a set of buttons embedded in a portion of the wearable strap spaced away from the first cavity, the set of buttons being configured to initiate dispensing of the treatment substance from the deformable cartridge when actuated.

11 Claims, 10 Drawing Sheets

10
25
90
17
22
14
20
19
16

(56) References Cited

U.S. PATENT DOCUMENTS 8,286,834 B2 * 10/2012 Powers ..................... A45F 5/00 222/175
8,844,766 B2 9/2014 Zaima et al.
8,902,713 B2 12/2014 Alameh et al.
9,848,828 B2 * 12/2017 Wisbey ................ A61B 5/4812
10,028,624 B1 * 7/2018 Robinson ............. A47K 5/1201
10,646,162 B2 * 5/2020 Jeong .................... G06F 1/1684
2003/0234726 A1 * 12/2003 Chen .................... A61B 5/0008 340/573.1
2008/0151695 A1 * 6/2008 Kimel .................... G04B 47/00 368/10
2009/0069642 A1 * 3/2009 Gao ........................ H04L 67/12 600/300
2009/0177068 A1 * 7/2009 Stivoric ................. A61B 5/002 600/365
2009/0322513 A1 * 12/2009 Hwang ................ G08B 25/016 340/539.12
2011/0155765 A1 * 6/2011 Properzi .............. A47K 5/1201 222/175
2012/0282011 A1 11/2012 Francois
2013/0014312 A1 * 1/2013 Izkovitz ............... A44C 9/0069 2/160
2013/0261415 A1 * 10/2013 Ashe .................. A61B 5/14552 600/324
2013/0334248 A1 12/2013 Iseri et al.
2014/0117060 A1 * 5/2014 Colone .................. A44C 5/003 224/219
2015/0094544 A1 * 4/2015 Spolin .................. A61B 5/6831 600/301
2015/0100245 A1 * 4/2015 Huang ................. A61B 5/1123 702/19
2015/0119198 A1 * 4/2015 Wisbey ................ A61B 5/1455 482/9
2015/0120203 A1 * 4/2015 Wisbey ................ A61B 5/4815 702/19
2015/0216367 A1 8/2015 Barbier
2015/0268718 A1 * 9/2015 Fujii ..................... G06F 1/1684 340/5.51
2015/0305675 A1 * 10/2015 Miller .................. A61B 5/7246 600/301
2015/0382105 A1 * 12/2015 Thompson ............. A61B 5/681 381/94.1
2016/0045172 A1 * 2/2016 Aratani .................. A61B 5/681 600/595
2016/0342767 A1 * 11/2016 Narasimhan ............ G06F 19/00
2017/0150930 A1 * 6/2017 Shikii .................... A61B 5/026
2017/0156454 A1 6/2017 Abadi et al.
2017/0184523 A1 * 6/2017 Ikeda ..................... G01K 13/20
2018/0206682 A1 * 7/2018 Robinson ............... A47K 5/122
2018/0247713 A1 * 8/2018 Rothman ............... G16H 50/30
2018/0330811 A1 * 11/2018 Macary .................. G16H 20/70
2019/0099613 A1 * 4/2019 Estes .................... A61B 5/0071
2020/0060545 A1 * 2/2020 Maher .................. A61B 5/0022
2020/0245822 A1 * 8/2020 Chacon, Jr. .......... A44C 5/0007

* cited by examiner

WEARABLE HEALTH AND TREATMENT DEVICE

BACKGROUND

Proper sanitization is important as a disease control measure in a variety of industries. The CDC estimates that about 1.7 million infections occur each year, one fourth of which are attributable to improper hand sanitization compliance in industries such as healthcare, food service and restaurants, schools and childcare, and mass gatherings and conventions. Hand hygiene compliance management is important in hospitals given the risk of hospital-acquired infections. Reinforcement and improvement of hand hygiene standards is especially important where health caregivers may touch multiple patients each day with various contagions, potentially serving as a vector for the transmittance of multiple contagions. This is of particular concern because many hospitals lack hand hygiene compliance auditing tools, such as hand hygiene ledgers or records. In such hospitals there may be no accountability or reinforcement devices for healthcare providers. Interaction with patients is necessary to some who may be immunosuppressed, or in-patient recovery rooms where infection may thrive. Katherine Ellingson, Ph.D., an epidemiologist at the CDC, has highlighted hand hygiene issues based on researched and identification of healthcare-associated infection risks through improper hand hygiene compliance. Infections from hand hygiene non-compliance still occur despite training initiatives, signage, and the convenient placement of handwashing sinks and sanitization stations in the industries where hand hygiene is important. This costs hospitals, institutions, governments, and society tens of billions of dollars yearly in preventable healthcare costs and early deaths.

A major concern in the healthcare industry, and of particular importance to hospitals, are readmission rates. Under Medicare and other legislation, government regulations incentivize hospitals to reduce readmissions by placing the cost burden of readmissions on the attending medical facility. From a compliance and prevention manager's perspective, providing convenient and easier methods and systems, or devices, to perform a routine treatment task generally means healthcare providers will perform the task more frequently. One objective of the invention is to enhance and change poor hand hygiene behavior to reduce infections and thereby reduce readmission rates.

Presently, many treatment substances, e.g., hand and body lotions, sunscreen protection, mosquito repellent, hand sanitizer, and liquid soaps, are typically sold in squeeze containers in order to dispense and apply a treatment substance. In the past other products such as sunscreen have been sold in bottles with a hand pump, or as a powder in a tube with a brush, or as an aerosol in a pressurized can with a nozzle. However, these containers and dispensers are not necessarily convenient. The bottles and containers are frequently dark or colorful and do not show clearly when the substance is used up, sometimes making a user feel reluctant to use the container because it may not contain enough treatment substance. Moreover, the containers are easy to lose or forget, e.g., in a car, cabinet, locker, or accidentally left somewhere in public. This can cause a user such as a healthcare provider, patient, or other user, to not adhere or apply the desired or needed treatment substance or take prescribed medication. For example, a user could misplace a sunscreen, pill or sanitizer bottle and then would forgo using sunscreen, or forgo taking medication, or sanitizing hands. Consequently, there is a need for a wearable health and treatment device that clearly indicates to a wearer the level of treatment substance remaining. Further, there is a need to separate the container of the treatment substance from a wearable dispenser, thereby allowing for replacement cartridges of the treatment substance.

Besides hand hygiene compliance, another fundamental health protocol is regular monitoring of one's body temperature. A person's body temperature—that is the presence of absence of a fever—is an important indicator of health. Typically, one's body temperature is 98.6° F., to within a typical variation of +/−1° F. The raising of one's body temperature above the normal temperature range associated with homeostasis is indicated for myriad illnesses. Thus, fever is one of the most ubiquitous clinical indicators looked for during evaluation for infectious diseases.

Specific current world events have even further emphasized the importance of monitoring one's body temperature as an indicator of overall health. For example, travelers returning from countries with widespread COVID-19 transmission are typically advised to take and monitor their body temperatures twice a day. Notably, COVID-19 has also changed the way in which people comport themselves in social environments. Social distancing is now a normal health protocol for interacting with others. Moreover, social distancing and other health protocols have increasingly dictated that people adhere to strict personal and professional hand sanitization regimens. Therefore, there exists a need for a wearable health and treatment device having embodiments which are configured to detect and display a wearer's body temperature or dispense a treatment substance so as to further facilitate adherence to an overall health regimen.

BRIEF SUMMARY

Systems, methods, and apparatuses for a wearable health and treatment device are disclosed. In accordance with one aspect, a wearable sanitizing system is provided. In some embodiments, the wearable sanitizing system comprises a wearable strap. The wearable strap of various embodiments has a first cavity extending along a portion of the wearable strap. In some embodiments, the wearable sanitizing system further comprises a deformable cartridge positioned substantially within the first cavity and is configured to contain and selectively dispense a treatment substance. In some embodiments, the wearable sanitizing system further comprises a body temperature capturing component. One side of the body temperature capturing component of various embodiments is in contact with a portion of a wearer's skin, and an opposing side of the body temperature capturing component is in contact with the deformable cartridge. In some embodiments, a set of buttons is embedded in a portion of the wearable. The set of buttons of various embodiments is spaced away from the first cavity and is configured to initiate dispensing the treatment substance from the deformable cartridge when actuated. In some embodiments, the wearable sanitizing system further comprises a processor embedded in the wearable strap. The processor of various embodiments is configured in operable communication with the body temperature capturing component and the deformable cartridge for receiving data from the body temperature capturing component and the deformable cartridge, and for transmitting the received data over a network to a distributed computing device remotely located relative to the wearable strap.

In some embodiments, the wearable strap further comprises a display configured to indicate diagnostic information including at least an amount of the treatment substance contained within the deformable cartridge, and a body temperature of a wearer.

In some embodiments, the diagnostic information indicates that the deformable cartridge may be discarded.

In some embodiments, the diagnostic information further includes an allowed temperature indicator that indicates that the body temperature of the wearer is within an allowed temperature range. The allowed temperature indicator of various embodiments is chosen from the group consisting of a visual indicator, an audible indicator, a tactile indicator, and a composite indicator.

In some embodiments, the diagnostic information further includes a disallowed temperature indicator that indicates that the body temperature of the wearer is not within an allowed temperature range. The disallowed temperature indicator of various embodiments is chosen from the group consisting of a visual indicator, an audible indicator, a tactile indicator, and a composite indicator.

In accordance with one aspect, a method of using a wearable device is provided. In some embodiments, the method comprises dispensing a treatment substance from a deformable cartridge. In some embodiments, dispensing includes actuating a set of buttons embedded in a strap. In some embodiments, the method comprises detecting a body temperature of a wearer. In some embodiments, the method comprises displaying the detected body temperature of the wearer. In some embodiments, the method comprises transmitting diagnostic information regarding the amount of treatment substance contained in the deformable cartridge or the body temperature of the wearer over a network.

In some embodiments, the step of detecting a body temperature of a wearer occurs automatically in compliance with one or more predetermined protocols.

In some embodiments, the step of detecting a body temperature of a wearer occurs periodically in compliance with one or more predetermined protocols.

In some embodiments, the step of dispensing a treatment substance is performed prior to entry into an environment having health protocols in place.

In some embodiments, the step of displaying the detected body temperature is performed prior to entry into an environment having health protocols in place.

In some embodiments, the step of detecting the body temperature of the wearer is automatically initiated upon engaging of the wearable device on the wearer's person.

In some embodiments, the method further comprises the step of providing an initial sanitation alert.

In some embodiments, the method further comprises the step of transmitting a termination alert that the wearable device has been removed.

In accordance with one aspect, a wearable device is provided. In some embodiments, the wearable device comprises a wearable strap. The wearable strap of some embodiments has a first cavity extending along a portion of the wearable strap. In some embodiments, the wearable device further comprises a deformable cartridge positioned substantially within the first cavity and is configured to contain and selectively dispense a treatment substance. In some embodiments, the wearable device further comprises a body temperature capturing component. One side of the body temperature capturing component of various embodiments is in contact with a portion of a wearer's skin, and an opposing side of the body temperature capturing component is in contact with the deformable cartridge. In some embodiments, a set of buttons is embedded in a portion of the wearable. The set of buttons of various embodiments is spaced away from the first cavity and is configured to initiate dispensing the treatment substance from the deformable cartridge when actuated.

In some embodiments, the body temperature capturing component comprises a flexible substrate having sensing elements embedded therein.

In some embodiments, the sensing elements are embedded in the flexible substrate at a concentration of 1 per $cm^2$, 2 per $cm^2$, or 5 per $cm^2$.

In some embodiments, the body temperature capturing component comprises a temperature sensing portion having a size corresponding with a size of an opening of the first cavity defined by the strap.

In some embodiments, the strap comprises a material that is resistant to microbe growth.

In some embodiments, the wearable device further comprises a removable encasing portion. The removable encasing portion of various embodiments is configured to removably engage the first cavity defined by the strap and encase the deformable cartridge and the body temperature capturing component therein.

In some embodiments, the removable encasing portion comprises a material that is resistant to microbe growth.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF VARIOUS EMBODIMENTS

Various embodiments of the present invention now will be described more fully hereinafter with reference to the accompanying drawings, in which some, but not all embodiments of the invention are shown. Indeed, these inventions may be embodied in many different forms and should not be construed as limited to the embodiments set forth herein;

rather, these embodiments are provided so that this disclosure will satisfy applicable legal requirements. The term "or" (also denoted "/") is used herein in both the alternative and conjunctive senses, unless otherwise indicated. The terms "illustrative" and "exemplary" are used to be examples with no indication of quality level. Like numbers refer to like elements throughout.

Figure 1:
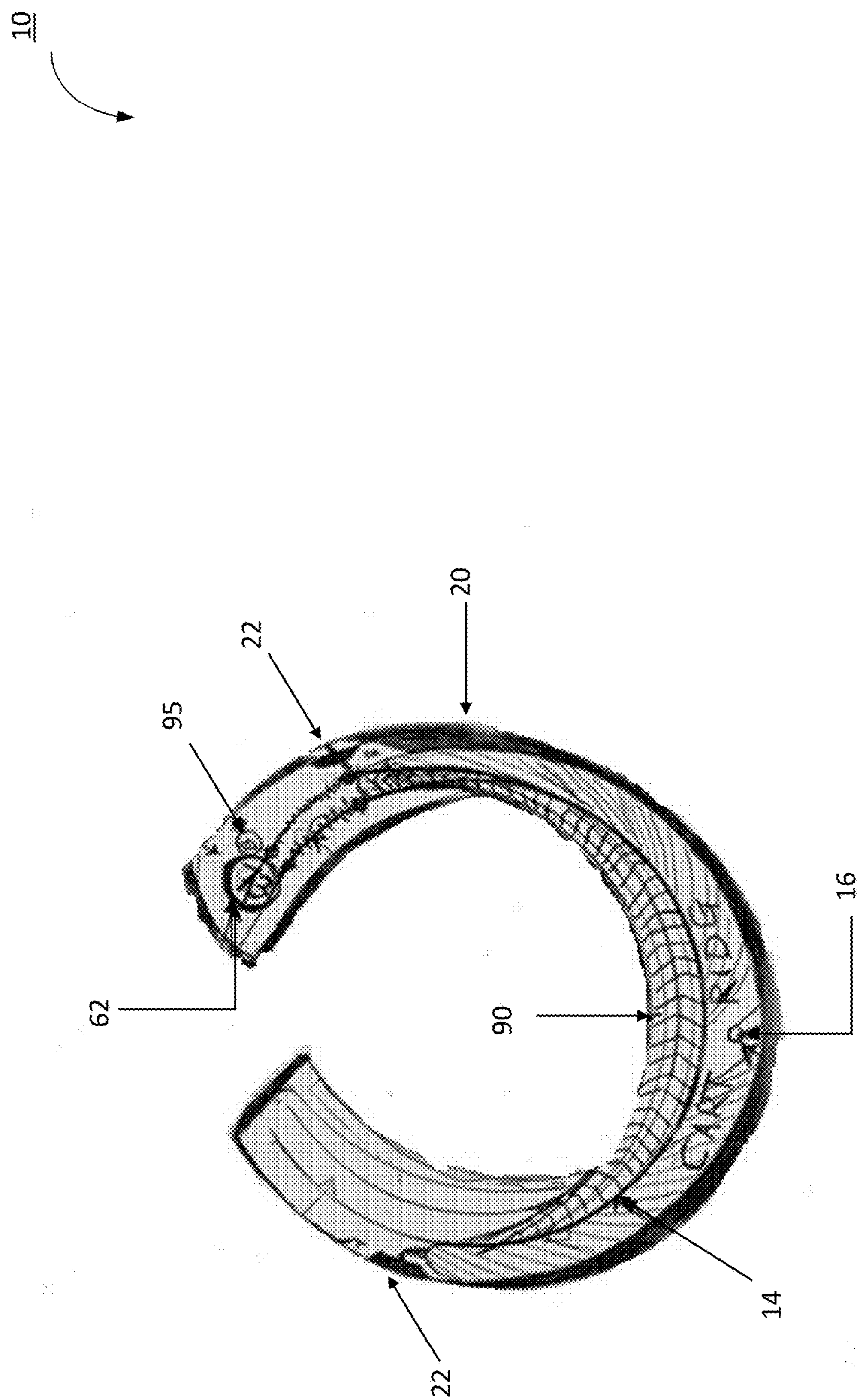
FIG. 1 illustrates a top view of a wearable health and treatment device comprising a body temperature capturing component according to various embodiments.
Figure 2:
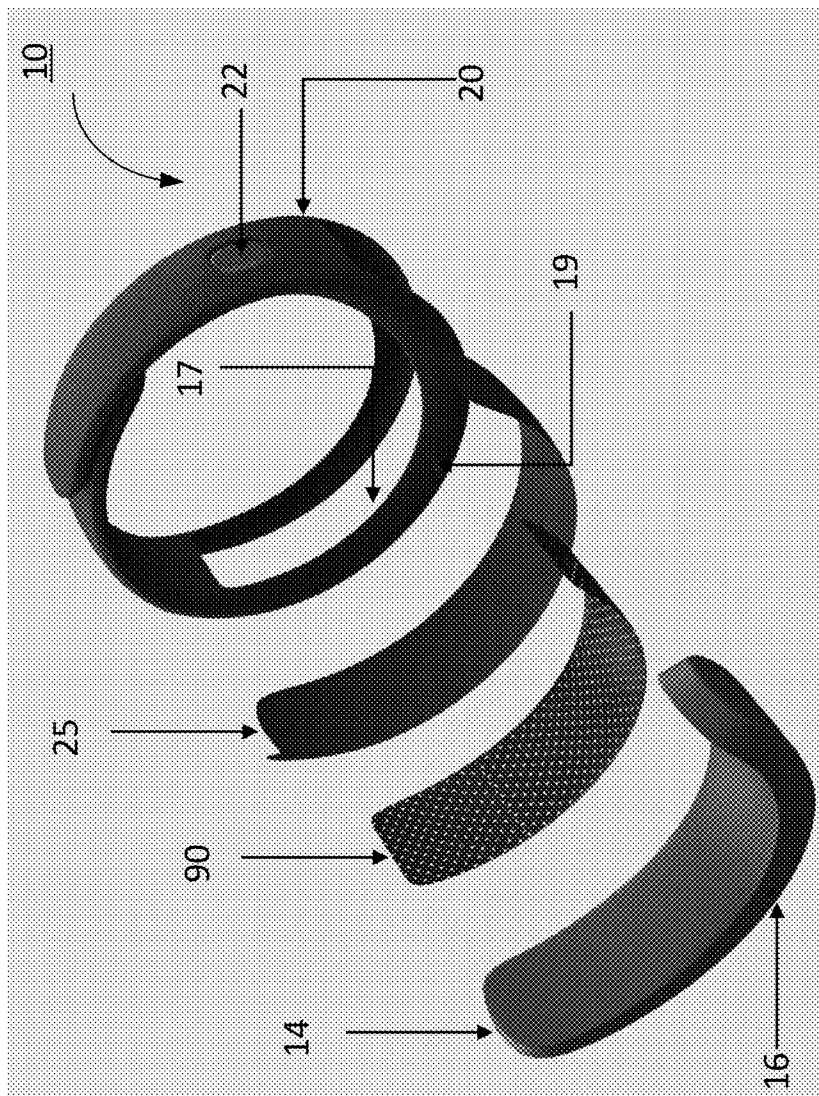
FIG. 2 illustrates an exploded view of a wearable health and treatment device comprising a body temperature capturing component according to various embodiments.
Figure 3:
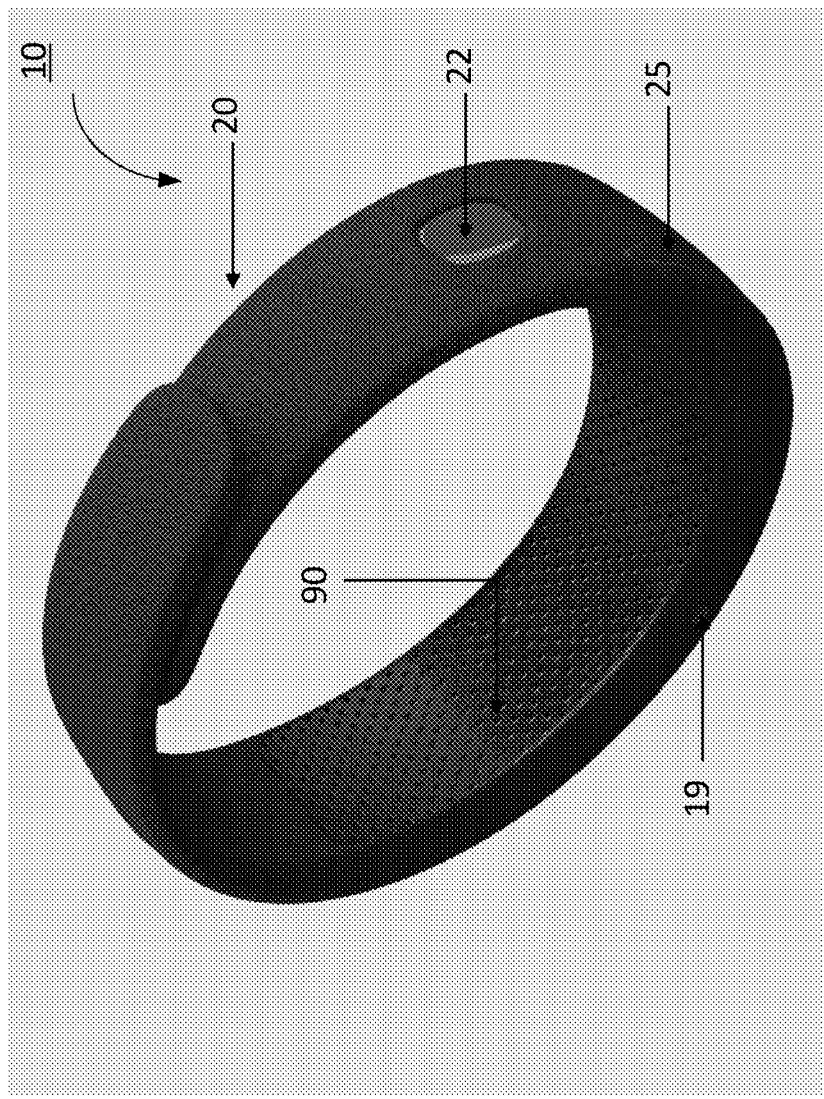
FIG. 3 illustrates a perspective view of a wearable health and treatment device comprising a body temperature capturing component according to various embodiments.

1. First Set of Exemplary Embodiments of the Wearable Health and Treatment Device In the exemplary embodiments as illustrated in FIGS. 1-3, the strap 20 may comprise one or more sensors (not shown) or data capturing components configured to detect and send or otherwise transmit data or physiological information to the computing device 62, the main display 74, and/or a remotely distributed computing device. Moreover, the computing device 62 may comprise at least a processor (not shown) that is embedded in the strap 20 and configured in operable communication with the data capturing component and the deformable cartridge 14 for receiving data from the data capturing component and the deformable cartridge 14, and for transmitting the received data over a network to the remotely distributed computing device.

A sensor or data capturing component of various embodiments may be configured to detect and transmit a variety of available physiological information, including but not limited to, body temperature, heart rate, breathing rate, or number of steps taken. In the depicted embodiment, the data capturing component is a body temperature capturing component 90 configured at least to detect and transmit to the computing device 62 a user's external body temperature. The body temperature capturing component 90 may thus comprise a flexible or otherwise pliable substrate of material configured to be worn either on the top or on the bottom of a wearer's wrist. The substrate material is ergonomically configured to engage all possible wrist sizes in order to detect an external body temperature of any wearer. For example, the body temperature capturing component 90 may comprise silicon rubber, thermoplastic rubber, etc. In some embodiments, the body temperature capturing component 90 comprises a material that is resistant to microbe growth. In some other embodiments, the substrate of the body temperature capturing component 90 comprises the same flexible material as the strap. In yet still some other embodiments, the substrate of the body temperature capturing component 90 comprises a disposable material. Thus, the body temperature capturing component 90 of various embodiments comprises a hygienic or otherwise sterile and ergonomic substrate.

FIG. 1 illustrates a top view of an embodiment of the invention. In the depicted embodiment, the wearable health and treatment device 10 is configured so that a plurality of deformable cartridges 14 are juxtaposed between the body temperature capturing component 90 and an inner surface of the strap 20. As shown, there are a set of buttons 22 (here, a first button and a second button) embedded in a portion of the strap 20 and spaced away from the first cavity 17, and a nozzle 16 spaced apart from each of the buttons 22 that is integral with the plurality of deformable cartridges 14 and configured to dispense a treatment substance. The depicted embodiment is configured so that the set of buttons 22 (i.e., the first button and the second button) must be pressed together to release said treatment substance from said plurality of deformable cartridges 14. The depicted wearable health and treatment device 10 illustrates that the computing device 62 (discussed further below with reference to FIG. 9) is operably connected to the plurality of deformable cartridges 14 via leads 64, and to a battery 95. Thus configured, the computing device 62 may determine a plurality of levels of treatment substance within said deformable cartridges 14 and transmit or otherwise deliver such diagnostic information to the main display 74 for display thereon.

In some embodiments, the main display 74 is configured to indicate to a wearer or other observer that the wearer's body temperature is within an allowed temperature range, i.e., that the wearer's body temperature contraindicates a particular disease or diseases or any general unhealthiness. For example, the main display 74 may be configured to convey an allowed temperature indicator that indicates the wearer's body temperature is within an allowed temperature range. An allowed temperature indicator may be a visual indicator such as a first color (e.g., green), a first icon (e.g., "thumbs up" or "smiley face" or "check-mark") or other visual conveyance of information conducive for conveying that the wearer's body temperature is allowable. In other embodiments, the main display 74 is configured to convey to a wearer or other observer that the wearer's body temperature is not within an allowed temperature range. That is to say that, the wearer's body temperature indicates a particular disease or diseases or general unhealthiness. For example, the main display 74 may be configured to convey a disallowed temperature indicator, distinct from the allowed temperature indicator, that indicates the wearer's body temperature is not within an allowed temperature range. The disallowed temperature indicator of some embodiments may thus be a second visual indicator such as a second color (e.g., red), a second icon (e.g., "thumbs down" or "sad face" or "x-mark") or other visual conveyance of information conducive for conveying that the wearer's body temperature is not allowable.

In other embodiments, the allowed temperature indicator and disallowed temperature indicator may be audible indicators, tactile indicators or any other type of indicator configured to convey information. For example, in various embodiments, the main display 74 may further comprise audio circuitry configured to convey an audible indicator (e.g., a beep, buzz, hum, whistle or the like) that conveys that the wearer's body temperature is or is not within an allowed or acceptable temperature range. The main display 74 of still other embodiments may comprise tactile circuitry configured to generate a palpable or otherwise tactile sensation (e.g., a vibration, pulse, or the like) that conveys that the wearer's body temperature is or is not within an allowed or acceptable temperature range. Further, either of the allowed temperature indicator or the disallowed temperature indicator of certain embodiments may be configured as a composite indicator. That is, either or both of the allowed temperature indicator and the disallowed temperature indicator may comprise one or more types of indicators. For example, an allowed temperature indicator may comprise a first visual indicator and a first audible indicator (e.g. a check mark accompanied by a pleasant "ding" tone). Alternatively, a disallowed temperature indicator of this example embodiment may comprise a second visual indicator and a second audible indicator such as an x-mark accompanied by a harsh piano chord. An allowed temperature range may be determined according to known medical and physiological methods and/or health protocols.

In various embodiments, the substrate of the body temperature capturing component 90 comprises sensing elements such as thermistors, thermocouples, thermopiles, or the like, embedded within the substrate. In some embodiments, multiple pairs of sensing elements may be configured in electrical communication so that temperature differentials between pairs of sensing elements induce corresponding differentials in voltage, current, or other useful electrical and/or chemical signals. For example, a sum total of induced voltage differentials may be an output voltage that is used to indicate a wearer's body temperature (e.g., visually on the main display 74.) Thus, the sensing elements embedded in the flexible substrate of the body temperature capturing component 90 may be configured in electrical communication with the computing device 62 so as to transmit to the computing device 62 the output signal. The computing device 62 may accordingly be configured to receive the transmitted output signal and interpret or otherwise process the output signal and display the same as a body temperature of a wearer on the main display 74.

FIG. 2 illustrates an exploded view of an embodiment of the invention. In the embodiment depicted in FIG. 2, there is a button 22 embedded in the strap 20, and a nozzle 16 spaced apart from the button 22 that is integral with the cartridge 14 and configured to dispense a treatment substance. The depicted strap 20 defines a first cavity 17 configured to removably house the body temperature capturing component 90 and secure a deformable cartridge 14 in the strap 20. The first cavity 17 extends along a portion of the strap 20. In the depicted embodiment, the first cavity 17 is centered along the length of the strap 20. In other embodiments, the first cavity 17 may be configured off-center of the strap 20 so as to be aligned closer one side of the strap 20 than to the other.

The depicted strap 20 defines a second cavity 19 that is configured to allow the treatment substance to be dispensed therethrough. In the depicted embodiment, the wearable health and treatment device 10 further comprises a removable encasing portion 25. The removable encasing portion 25 is configured to removably engage the first cavity 17 defined by the strap 20 and encase the body temperature capturing component 90 and the deformable cartridge 14 therein. The depicted body temperature capturing component 90 and the deformable cartridge 14 are each configured to be flexibly disposed within the first cavity 17 defined by the strap 20, so that the strap 20 ergonomically contours the wrist of a wearer when the body temperature capturing component 90 and the deformable cartridge 14 are in place.

In certain embodiments, the sensing elements are embedded within the substrate at various advantageous spacing configurations. For example, the substrate of the body temperature capturing component 90 may be configured having any of several advantageous sensing element concentrations about its surface such as 1 sensing element per $cm^2$, 2 sensing elements per $cm^2$, 5 sensing elements per $cm^2$ or another advantageous sensing element concentration. Thus, economics may be served if, for example, sensing elements of lower resolution must be used.

The substrate of the body temperature capturing component 90 may alternatively be configured having a temperature sensing portion. In these example embodiments, a temperature sensing portion may be configured such that sensing elements are embedded within only a predetermined fraction of the substrate surface area. The strap 20 is thus configured so that the first cavity 17 defined by the strap 20 allows at least a portion of the body temperature capturing component 90 to contact a wearer's skin. For example, in the depicted embodiment, the strap 20 defines a first cavity 17 of the same or nearly the same dimensions as the body temperature capturing component 90. However, in various embodiments, the strap 20 defines a first cavity 17 of the same or nearly the same dimensions as only the temperature sensing portion of the body temperature capturing component 90. When the body temperature capturing component 90 is configured having a temperature sensing portion, the predetermined fraction of the substrate surface may coincide with a window or cavity defined by the strap 20 so that only the temperature sensing portion of the flexible substrate contacts a wearer's skin. That is to say that, the temperature sensing portion may be configured having a size corresponding with a size of the opening of the first cavity 17 defined by the strap 20. For example, the strap 20 may define a cavity having a profile or outline (e.g., a circular cavity, a rectangular cavity, etc.) that overlays or coincides with the temperature sensing portion. The strap 20 of some embodiments may further comprise the main display 74 (not shown), in order to display the data captured by the body temperature capturing component 90 or other diagnostic data.

FIG. 3 illustrates a perspective view of an embodiment of the invention. Particularly, FIG. 3 shows the deformable cartridge 14 (not clearly visible) and the body temperature capturing component 90, described above with reference to FIG. 2, housed within the first cavity 17 (not clearly shown) defined by the strap 20. In the depicted embodiment, the wearable health and treatment device 10 is configured so that the deformable cartridge 14 is juxtaposed between the removable encasing portion 25 and the body temperature capturing component 90. Thus configured, the second cavity 19 defined by the strap 20 overlays or otherwise coincides with the nozzle 16, so as to facilitate dispensing of the treatment substance from the deformable cartridge(s) 14. The removable encasing portion 25 is configured so that when engaged with the strap 20, the removable encasing portion 25 is oriented toward a dorsal aspect of the wearer, e.g., toward a dorsal aspect of the wearer's wrist. The body temperature capturing component 90 is configured so that when engaged with the strap 20, the sensors of the body temperature capturing component 90 contact at least a portion of the palmar aspect of the wearer, i.e., the palmar aspect of the wearer's wrist.

In various embodiments, the flexible substrate may further comprise one or more adhesive portions. For example, one or more adhesive portions of the flexible substrate may be defined on portions of the flexible substrate that are not configured for detecting a body temperature of a wearer. The one or more adhesive portions may be one or more surfaces or portions of surfaces of the flexible substrate having adhesive applied thereon. The adhesive is any one or more adhesives, as known, that are suitable to maintain adhesion of the flexible substrate to an inner surface of the strap 20. Thus, a body temperature capturing component 90 according to the present disclosure is configured to promote accurate temperature detection despite jostling, dislodging or the like.

Figure 4:
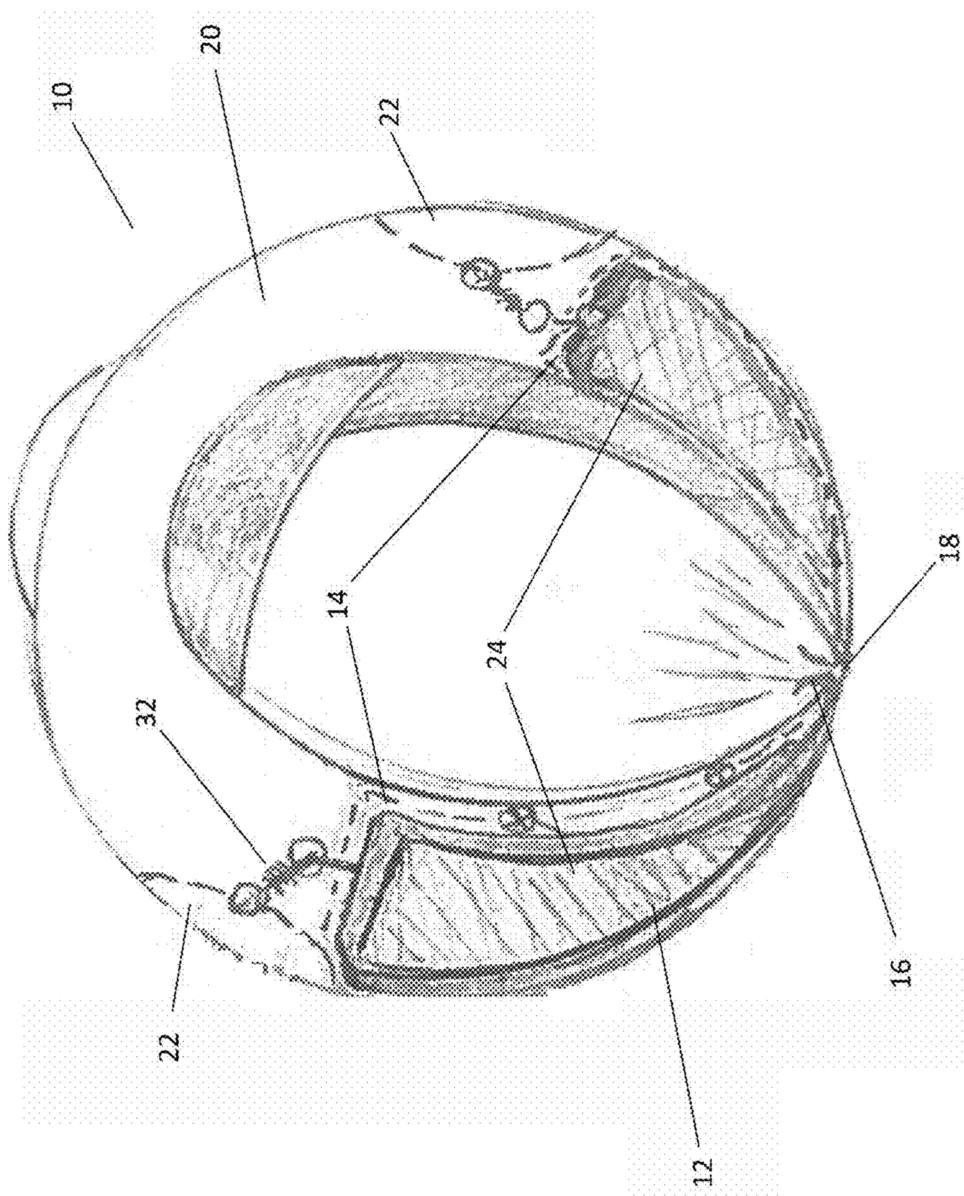
FIG. 4 illustrates a perspective view of a wearable health and treatment device according to various embodiments.

2. Second Set of Exemplary Embodiments of the Wearable Health and Treatment Device FIG. 4 illustrates a perspective view of a wearable health and treatment device 10 according to various embodiments. A strap 20 allows this embodiment to be worn by a wearer e.g., on the wearer's wrist. A treatment substance dispenser 12 is shown with conjoined cartridges 14, a nozzle 16, and a backflow ring 18. In a typical use of the invention, a person would attach the strap 20 to his or her person. For example, the wearable health and treatment device 10 may be worn on a wearer's wrist with the nozzle 16 generally directed towards the palm of the hand. It is understood that the treatment substance dispenser 12 can apply many forms of substances including but not limited to liquids, aerosols, pastes, creams, and solids such as but not limited to pills, capsules, and powders. It is also understood that the nozzle 16 may be configured to, upon actuation of two portions of the straps (shown as two buttons 22 in FIG. 1), dispense, release, or otherwise provide output for a treatment substance in any of these forms. In certain embodiments, the nozzle 16 will be attached to a cartridge (or to conjoined cartridges 14 as in FIG. 4) containing treatment substance, as discussed below. The nozzle 16 is usually oriented at around a 90-degree angle so that it may dispense substance towards or onto a user's palm. Depending on the angle of the nozzle 16, a user may need to bend his or her palm slightly and immediately prior to actuation so that the nozzle 16 would direct the treatment substance towards and onto at least a portion the user's palm. Then the user could rub both of his or her hands together to properly apply the treatment substance—where the treatment substance is ethanol sanitizer, the method is effective at reducing over 99% of pathogens. Typically, the type and size of nozzle 16 used is dependent on the type of treatment substance and its physical properties.

The strap 20 is typically comprised of silicon rubber or another suitably flexible material. Suitably flexible materials include but are not limited to silicon rubbers, thermoplastic rubbers, etc. The strap 20 may comprise an ergonomic surface designed for the comfort of a user who is wearing the wearable health and treatment device 10 for long periods of time. In addition, the strap 20 may be comprised of a newly developed polymer material, or any other suitable material with a binding surface that prevents pathogens from accumulating on its surface so as to be resistant to microbe growth. (Microbe Adhesion Depends on Surface Stiffness; Researchers Craft Bacteria-Resistant Films, 52 MIT TECH TALK 27 (May 21, 2008)).

After securing the wearable health and treatment device 10 to his person using the strap 20, in this typical embodiment, a wearer may actuate the buttons 22 by pushing on them. In most embodiments, a set of buttons 22 must be pressed at the same time for sufficient pressure to cause the treatment substance dispenser 12 to dispense a treatment substance from the conjoined cartridges 14. The sufficient pressure required for a dispensation is determined in part by the size or diameter of an orifice in a backflow ring 18. Requiring a set of buttons 22 to be pressed for a dispensation reduces the potential for accidental dispensation. As will be described in further detail with other figures, upon pushing a button 22, a lever is actuated causing the cartridge to reversibly deform and compress and dispense the treatment substance. Pushing a button 22 also causes a spring 26 (shown in FIG. 5) to compress against a rigid portion that may be within the strap 20 or a cavity, and upon release of the button 22 the lever actuates back to its original position. Also, upon release of the button 22, assuming a dispensation occurred, then while the lever actuates back to its original position then certain embodiments of the backflow ring 18 allow a substance (typically air) to enter the cartridge 14 in place of the now-missing treatment substance that was just dispensed.

The conjoined cartridges 14 comprise two cartridges in the FIG. 4 embodiment. A cartridge is at least any of the canisters known in the art that may be actuated to dispense a substance, typically a fluid. In the embodiment in FIG. 4, the conjoined cartridges 14 comprise two cartridges that are fluid sacs 24 that may be reversibly deformed by an actuating lever or clamping mechanism. In a typical embodiment, the cartridge 14 fits or is secured within a cavity defined by the strap 20, or within a plurality of cavities for a plurality of cartridges 14, conjoined or otherwise.

Figure 5:
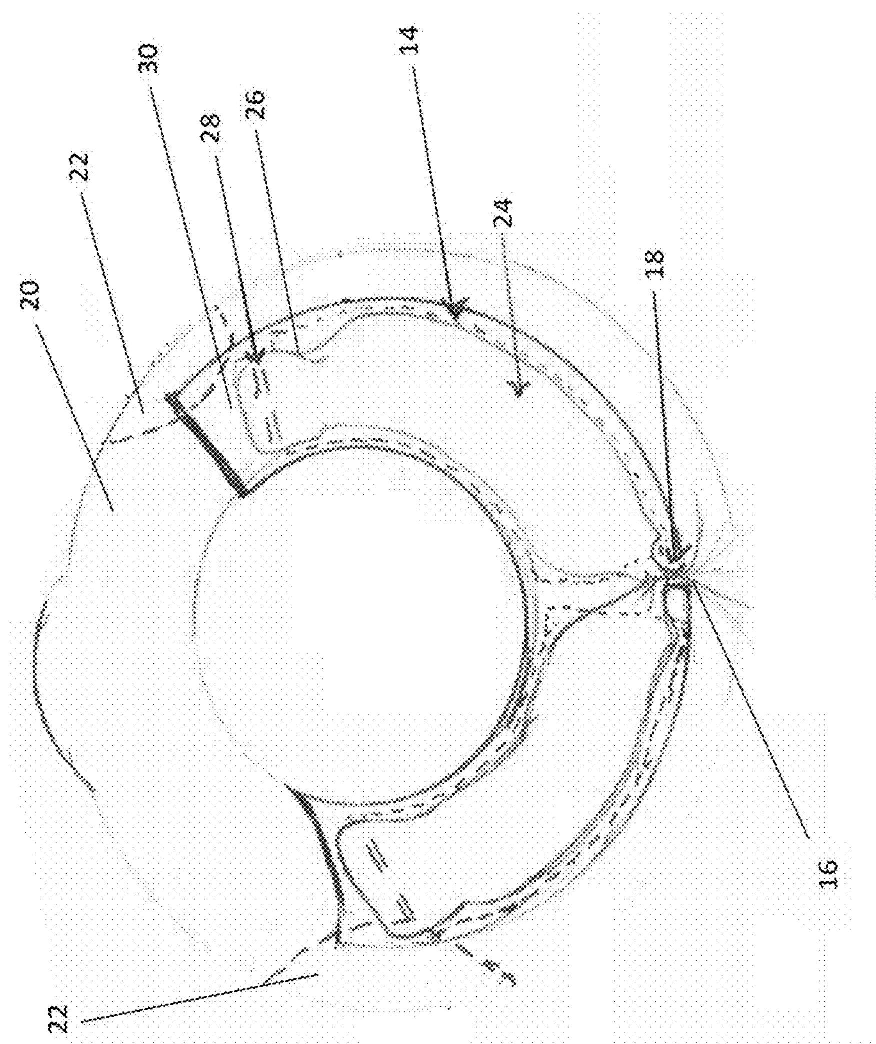
FIG. 5 illustrates a side view of a wearable health and treatment device according to various embodiments.

FIG. 5 illustrates a side view of a wearable health and treatment device 10 according to various embodiments. In the depicted embodiment, the cartridge 14 (indicated by a broken line) comprises a contour and/or a ridge 28 so that it may snap into place within a cavity 30 in the strap. Cartridges 14 may be replaced within the same cavity 30 by a refill cartridge that is similar to the previously described cartridge 14. In some embodiments the refill cartridge also comprises silicon rubber. To replace a cartridge 14, a user may remove it from the cavity 30 in the strap 20. After the cartridge 14 is removed from the cavity 30, it may be replaced by an appropriate cartridge of an appropriate treatment substance that will operate with the treatment substance dispenser 12 and nozzle 16 (if the nozzle is not also removed). Certain cartridge 14 embodiments will have integrated or attached nozzles 16 such that removal of the cartridge 14 would also remove the nozzle 16, and the replacement cartridge 14 in such an embodiment would also typically be understood to have a nozzle 16. Nozzles 16 could also be separate components and therefore separately designed and replaceable.

The cartridge 14, or conjoined cartridges 14, are further designed such that the nozzle 16 dispenses a fixed amount of treatment substance upon each actuation (e.g., approximately 2.8 mL for an ethanol sanitizer embodiment), and the cartridge 14 may be sized to contain certain total volumes of treatment substance. Therefore, a typical ethanol sanitizer with conjoined cartridges 14 would contain a total of 15 or 25 dispenses worth of ethanol sanitizer, or approximately 42 mL or 70 mL of ethanol sanitizer when approximately 2.8 mL is used for each dispense. Cartridges 14 may also be sized according to the size of the strap 20, which is separate from the total volume of treatment substance.

As shown in FIG. 5, in a typical embodiment, the cavity 30 containing a cartridge 14 typically extends into the sides of the strap 20. In such an embodiment, the actuation of the nozzle 16 occurs when a user puts pressure on the set of buttons 22. The user's pressure causes the silicon or other flexible material of the cartridge 14 to compress, causing displacement and/or pressure build-up in the substance and/or any of the air drawn inside the cartridge, and ultimately causing an amount of the substance to exit the nozzle 16 (usually approximately 2.8 mL) with a certain amount of velocity. In most embodiments, the velocity will be sufficient for the treatment substance to reach the palm of the user. In the embodiment in FIG. 5, with a conjoined cartridge 14 the user must put pressure on both buttons 22 at the same time in order to build up enough pressure inside the cartridge to cause a release of fluid through the backflow ring 18. Because both buttons 22 must be pressed this reduces the chance of accidental dispensing. The backflow ring 18 otherwise remains closed, although in some embodiments may let air through into the cartridge after dispensing, or another substance. In this embodiment, the fluid sacs 24, may extend out from the cartridges 14, and the cavity 30 is sized slightly larger than the fluid sacs 24 and the cartridges 14. In other embodiments the cavity 30 could be sized small or larger, and the cartridge may not contain a fluid sac 24 but rather a different internal component for containing a treatment substance. Also, the fluid sac 24 or other internal component for containing a treatment substance may not necessarily extend out from the cartridge 14.

Figure 6:
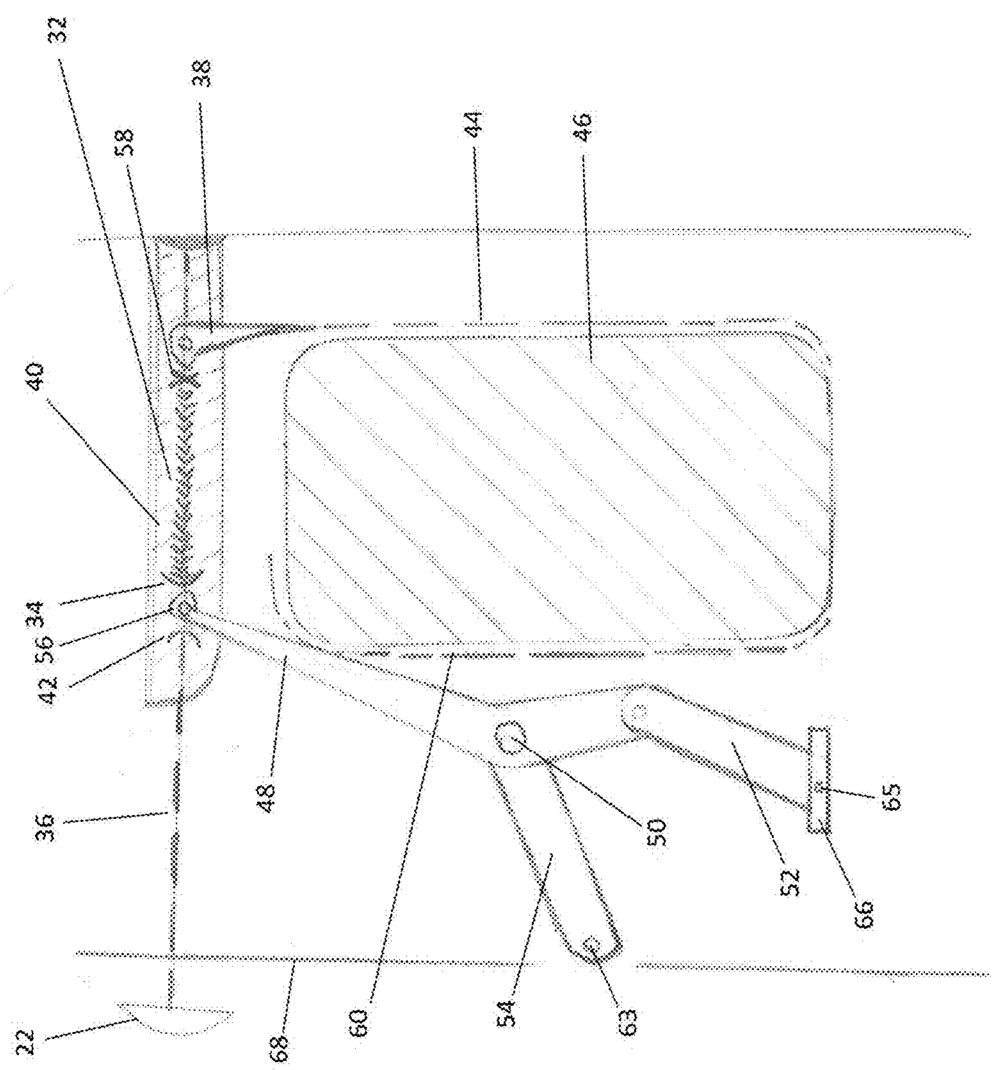
FIG. 6 illustrates an actuating portion of a wearable health and treatment device according to various embodiments.

FIG. 6 illustrates an actuating portion of a wearable health and treatment device 10 according to various embodiments.

Specifically, FIG. 6 shows an embodiment of the invention and its operation to reversibly deform cartridges 14 and dispense a treatment substance. FIG. 6 shows one cartridge 14 of an ethanol sanitizer solution embodiment. As in FIGS. 4 and 5, the user would press the button 22 and cause the cartridge 14 to deform and displace and/or pressurize the sanitizer solution in its container 46 within the cartridge. The container 46 could be a fluid sac 24 (described above with reference to FIGS. 4 and 5). Causing the cartridge 14 to deform could also displace and/or pressurize any other substance in the cartridge 14, such as air (similar to the operation of a consumer syringe bulb). While only one button 22 is shown in this figure, typically there would be two buttons 22 that would need to be pressed causing 2.8 mL of ethanol sanitizer to dispense, or flow out past the backflow ring 18 and out of the nozzle 16 with sufficient speed to reach the user's palm.

When the button 22 in FIG. 6 is pressed, a rod 36 moves causing a first washer 42 to move a first lever pivot 56. This movement causes at least a first lever arm 48 to actuate, and also causes a second washer 34 to compress a spring 32. The spring 32 compresses a third washer 58 against a rigid body 38 connected to a rigid backstop 44. The rigid body 38 does not move as the spring 32 is compressed or as the rod 36 is pushed. In this embodiment, the rod is pushed and passes through a spring housing 40. In this particular embodiment, as the button 22 is pressed, the first lever arm 48 actuates on the first lever pivot 56 and on a second lever pivot 50, causing a second lever arm 52 and a third lever arm 54 to also actuate, pushing against and beginning to deform the cartridge 14. The second lever arm 52 pivots around a second lever arm pivot 65, and the third lever arm 54 may pivot around a third lever arm pivot 63. The second lever arm 52 typically would pivot around the second lever arm pivot 65 which rotates within a second lever arm housing 66, and which is connected or anchored to the strap 20. Typically, the third lever arm pivot 63 will slide on or move adjacent to or in connection with a railing 68. In this embodiment these components, such as levers and pivots, will usually be comprised of metal, but other durable and rigid substances are also contemplated. The components will also usually fit within a cavity 30 in the strap 20 and would generally not be disposable.

The railing 68 is typically made of metal but could be any rigid or semi-rigid substance including plastics. In a typical embodiment the railing 68 is comprised within the strap 20. The railing 68 will typically be straight and will have two parallel portions extending substantially along its length to prevent a lever 7 from deviating from a controlled path. Upon actuation, the railing 68 will usually remain stationary and push back upon one or more levers, but it could be designed, in conjunction with the strap 20, to allow for some movement during actuation in connection with one or more levers pushing against it. In some embodiments the railing 68 could be curved to further control the motion of one or more levers to facilitate pressure applied through squeeze pads 60. In another embodiment the railing 68 could comprise a gear, chain, or chain-like or gear-like portions that serve to control the motion of one or more levers in connection with the railing. In still other embodiments the railing 68 could comprise ball bearings. Broadly, the configuration and embodiment of the railing 68 could be matched to a particular type, size, or style of cartridge, or to a cartridge that is designed for particular treatment substances where such a cartridge would have special requirements during actuation, e.g., increased leverage or compression against it to properly dispense for a cartridge using a dense powder.

FIG. 6 also shows squeeze pads 60 around the cartridge 14 where the lever or levers will engage to compress and reversibly deform the cartridge 14. When used, squeeze pads 60 are typically constructed of a rigid, pliable, or semi-pliable material that can exert pressure over a particular area. In one embodiment, the squeeze pads 60 are constructed of a tough fabric-like material such as a dense non-woven plastic. In other embodiments, the squeeze pads 60 will become denser upon compression and may be akin to a sponge-like material. In some exemplary embodiments, the squeeze pads 60 do not puncture, or irreversibly alter the cartridge 14. In some embodiments, the squeeze pads may be separate from a lever or levers, but in other embodiments the squeeze pads 60 are actually integrated into a lever or levers.

Figure 7:
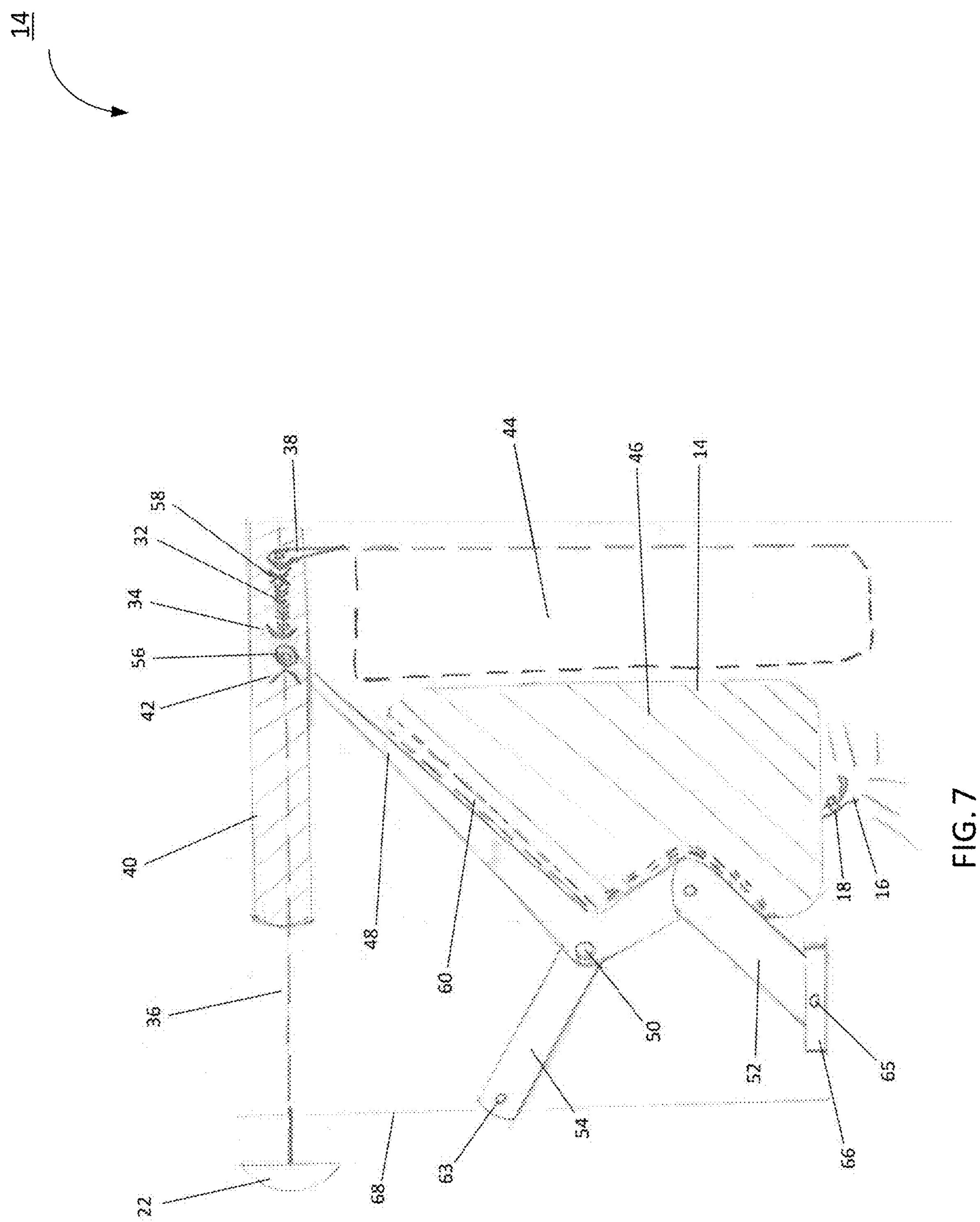
FIG. 7 illustrates an actuating portion of a wearable health and treatment device according to various embodiments.

FIG. 7 illustrates an actuating portion of a wearable health and treatment device 10 according to various embodiments. Here, the button 22 has been pressed, pushing the rod 36 into the spring housing 40, and causing two washers 42, 34 to actuate the first lever 48 while compressing the spring 32 against another washer 58 and a rigid body 38. As the levers actuate the first and second lever 48, 52 compress the squeeze pads 60, which compress the cartridge 14 and the container 46 within the cartridge.

In both FIG. 6 and FIG. 7, when the button 22 is released by the user, the spring 32 acts to snap back, i.e., return to its original state. This spring force causes the washers 34, 42, to push the rod 36 into the first lever pivot 56, thereby actuating the levers in reverse and releasing the pressure from the squeeze pads 60. This allows the cartridge 14 to reform after its deformed state, which is shown in FIG. 7. Releasing the button 22 also resets the embodied mechanism of FIGS. 6 and 7 for a subsequent dispensing. In some embodiments, as more and more treatment substance is dispensed, a user would need to push the buttons 22 deeper in order to actuate the levers to create sufficient pressure to dispense the correct amount of treatment substance. Such a configuration may be useful, for example, when the treatment substance to be dispensed comprises a compound that is contra-indicated or for which overexposure is undesirable. However, a feature of the backflow ring 18 is that after dispensing when the spring 32 is returning to its original position, or the squeeze pads 60 are releasing their pressure on the cartridge 14, then the backflow ring 18 can then allow a substance (typically air) to enter the cartridge 14 in place of the now-missing treatment substance that was just dispensed. The next time a user presses a button or buttons 22, the levers would cause the squeeze pads 60 to then push on air inside the cartridge 14, and the air would push out the treatment substance. In this embodiment, a user would not need to keep pressing deeper and deeper on the buttons 22 as more and more treatment substance left the cartridge 14. Thus, such a configuration may be desirable for applications that require uniform dispersal of a treatment sub stance.

The amount of fluid released, i.e., after, as in most embodiments, both buttons 22 are pressed and sufficient pressure is placed by the squeeze pads 60 onto the cartridge 14, can be optimized or controlled at least by calibrating or configuring any of the washers 34, 42, the first lever pivot 56, the rod 36, the squeeze pads 60, the spring 32, the cartridge 14, and substance container 46. In an example embodiment, wherein a treatment substance is a typical ethanol-based sanitizer, at least one of the washers 34, 42, the first lever pivot 56, the rod 36, the squeeze pads 60, the spring 32, the cartridge 14, and substance container 46 are configured such that a dispensing action will release 2.8 mL sanitizer from a conjoined cartridge.

It is understood that FIG. 6 and FIG. 7 only show certain embodiments of the invention and its lever mechanisms. Other levers understood in the art may be incorporated into different configurations to achieve certain advantages. For example, some embodiments may include lever(s) that slide on a rail or rails as does the third lever arm 54 in FIG. 6 and FIG. 7. Here, the minimal structure required to practice these embodiments is a single actuating lever, e.g., the first lever arm 48, that will serve to compress the cartridge 14 upon pressing a button 22.

Figure 8:
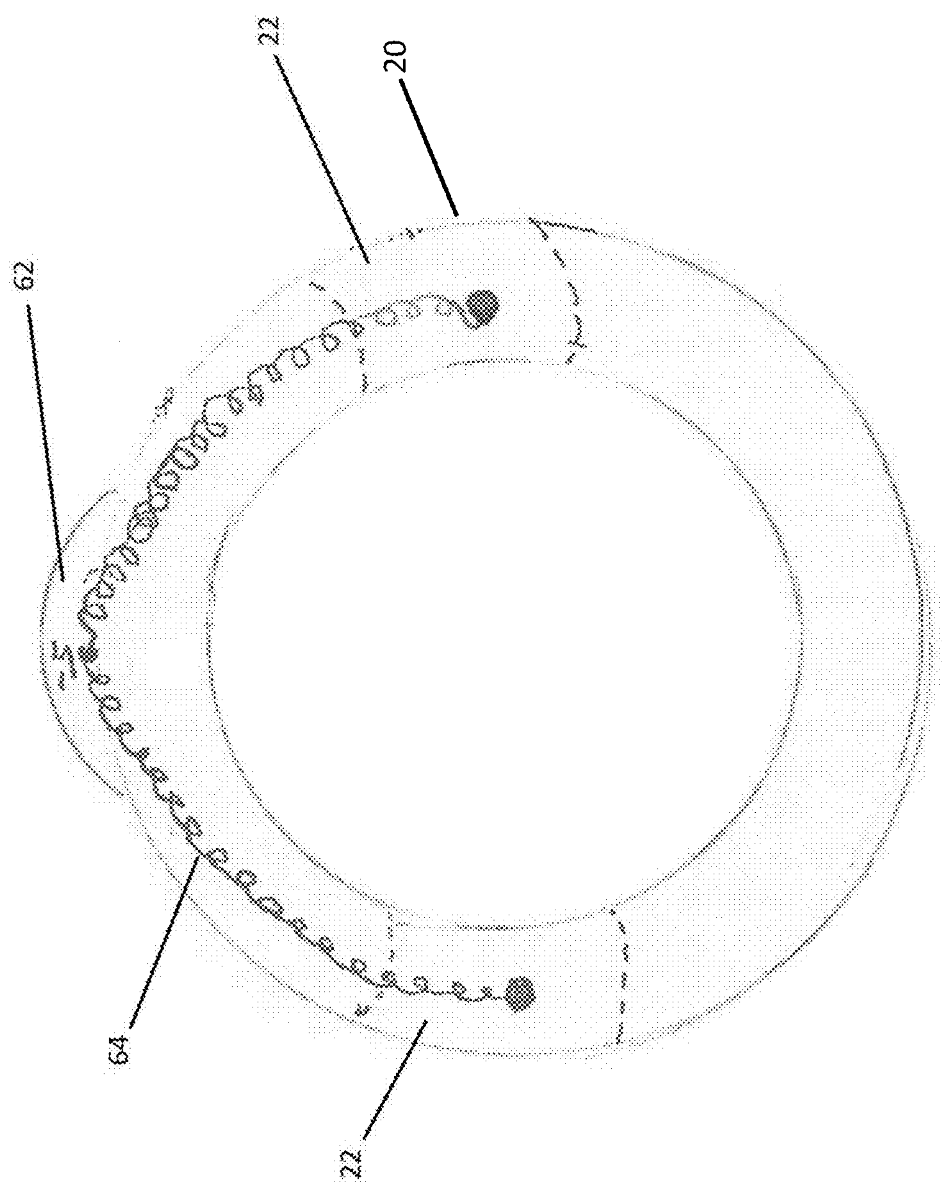
FIG. 8 illustrates leads in a wearable health and treatment device according to various embodiments.

FIG. 8 illustrates leads in a wearable health and treatment device 10 according to various embodiments. Further, the FIG. 8 embodiment comprises a computing device 62. In such embodiments, the actuation of the buttons 22 is detected by leads 64 in communication with the computing device 62 that extend down a portion of the strap 20 and/or the sides of the strap 20. In one embodiment, the leads 64 may connect near, on, or in the buttons 22 and an actuation of the buttons 22 would cause the leads 64 to close a circuit, thus indicating to the computing device 62 that a dispensation of treatment substance has occurred. As shown in this embodiment in FIG. 8, insulated leads 64 extend to both sides of the strap 20, and the circuit on both sides must be closed before the computing device 62 records or counts a dispensation of a treatment substance. This is because in typical, but not all, embodiments both buttons 22 must be pressed for a dispensation to actually occur. In some embodiments, the leads 64 may be pressure-based, optical-based or electrical-based and may be placed in different areas in the strap 20 or even inside the cartridge 14 (not shown) or container 46 (not shown). In these embodiments, the leads 64 could detect the spring 32 (not shown) compressing, or a lever actuating, or any of the movements that cause a compression of the cartridge 14 or container 46, or the actual compression of the cartridge 14 or container 46 itself, or a release of a treatment substance at the nozzle 16 (not shown) or at the backflow ring 18 (not shown), or in other locations within the embodiment where a POSITA would understand detection would be useful.

Figure 9:
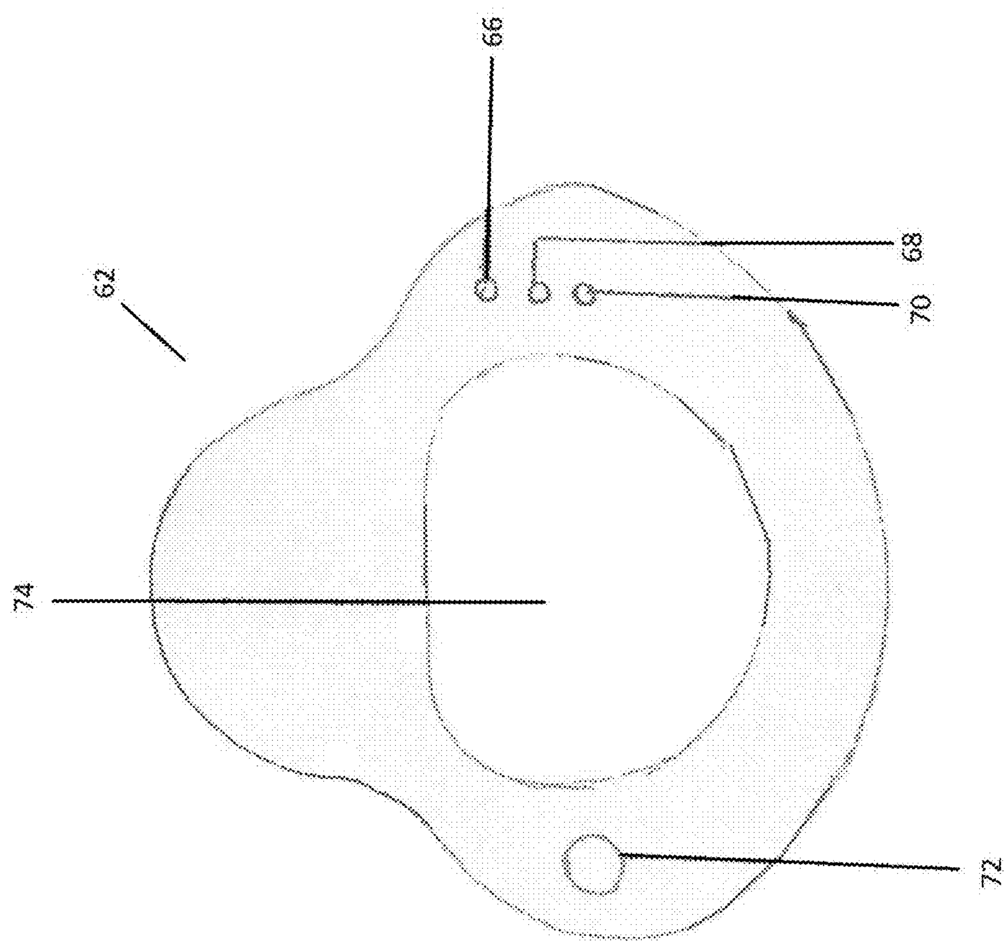
FIG. 9 illustrates a top view of a computing device of a wearable health and treatment device according to various embodiments.

FIG. 9 illustrates a top view of a computing device 62 of a wearable health and treatment device 10 according to various embodiments. For example, the computing device 62 may be used with the embodiments of the wearable health and treatment device depicted in any of FIGS. 1-8. The computing device 62 is typically affixed to the top of the strap 20 and the affixed computing device may be known as the crown. In a typical embodiment the computing device 62 is an Omega2 running the Linux operating system and operating off of Arduino hardware on a lithium battery (in a typical embodiment giving about 1-2 years of power). The computing device 62 is capable of wireless communication with other computing devices including Bluetooth and WiFi (e.g., 802.11 b/g/n, Cellular 2G/3G, Bluetooth 4.0, GPS expansions). The computing device 62 hardware may contain expansion docks, a cellular data expansion, an Arduino dock, a servo expansion, relay expansion, an organic LED (OLED) display or expansion, and a custom designed breadboard dock to be plugged into a breadboard expansion. The Linux operating system that the computing device 62 may use, may run many commercially available programming languages including Javascript, Python, Diamond, C++, Node, PHP, and many others. It may also operate as a server using, e.g., Apache, and is integrated with cloud computing, e.g., Onion Cloud. This allows remote control anywhere in the world with a real-time UI or RESTful API's. It also allows deployment of software updates in the field.

As discussed, the computing device 62 also detects when a user actuates the device to dispense a treatment substance—the leads that connect to the computing device 62 are not shown but would be present in this embodiment in a communications input/output port. The computing device 62 will determine, based on the total number of actuations, and the type and size of the cartridge 14, which it may detect or would be pre-programmed, how much treatment substance has been dispensed, and in turn how much treatment substance remains in the cartridge 14. In this typical embodiment, the computing device 62 may create an alert that a cartridge's 14 treatment substance is at a low level. This alert could be transmitted or indicated to anyone, including the user via one or more indicators 66, 68, 70, or wirelessly to any other computing device to which it is directly or indirectly connected.

The computing device 62 is understood to control the plurality of indicators 66, 68, 70 to indicate messages about the performance or connectivity of the computing device 62, including error messages, and also to indicate the status of data that the computing device 62 has received. Typically, the plurality of indicators 66, 68, 70 would take the form of LED lights, but could also include displays. The computing device 62 also typically includes a main display 74. The main display 74 is any display known in the art, and typically it comprises a high definition touch screen display such as those currently used on smartphones. In one exemplary embodiment, the main display 74 indicates diagnostic information including at least the level of treatment substance in the treatment substance dispenser 12, e.g., typically starting with the number of dispensations available or remaining in a cartridge 14, and reducing by one upon each actuation (or upon each determination by the computing 62 interpreting data sent from the leads 64). In some embodiments, the main display 74 further indicates certain physiological parameters including, but not limited to, a wearer's body temperature as discussed above with reference to FIGS. 1-3. A custom indicator 72 is another display that a user or manufacturer could program to indicate any number of configurations or any data received or in the memory of the computing device 62.

In one exemplary embodiment, the indicator 66 is configured to alert to the user such as a low-level warning, i.e., that a cartridge or a plurality of cartridges are at or near a level where replacement is recommended or critical for continued dispensation of treatment substance. In various embodiments, the indicator 66 is an optical indicator configured to emit a first light color (e.g., white light). In one exemplary, embodiment, the indicator 70 is an optical indicator configured to emit a second light color (e.g., red light) to indicate non-compliance. As an example, if a healthcare worker entered a room and was detected by a wireless device or motion detector near the doorway and did not actuate the dispenser within an actuation compliance time, an alert would be communicated to the dispenser causing a red light in the indicator 70 to illuminate. Similarly, the indicator 70 may illuminate if the user did not actuate the dispenser prior to leaving a room and such non-compliance was detected by devices in the room and communicated to the computing device 62. A red light would indicate non-compliance typically after an actuation compliance time passed and the healthcare worker still had not actuated the dispenser. In one exemplary embodiment, the indicator 68 is an optical indicator configured to emit a third light color (e.g., green light) that would indicate proper compliance when illuminated.

Extensions or add-ons to the computing device 62, connected to the strap 20, may vibrate or cause a sound for various levels of compliance or non-compliance instead of or in addition to illumination of the indicators 66, 68, 70. The custom indicator 72 may also be used to indicate compliance or non-compliance.

It is understood that the computing device 62 in FIG. 9 would also have a human interface (not shown), i.e., an interface used by a human to interact with the computing device 62. Human interfaces contemplated for this device include, without limitation: a button or set of buttons actuated by a user's finger to operate the computing device 62; a keyboard; a track ball or track-ball like device; a microphone or plurality of microphones; a touch screen or plurality of touch screens (including indicators 66, 68, 70, and 72 which could be touch screens), which may encompass a small or large portion, or all of the top portion of the crown of computing device 62. Any of the touch screens, including the main display 74, may be used to operate the computing device 62 to function as an entertainment device or gaming device, e.g., for children on vacation at the beach who bring an embodiment of the invention with them with a cartridge 14 containing sunscreen.

It is further contemplated that an optional access panel may provide a user with a way to replace a battery configured to power the computing device 62 or to replace the computing device 62 itself or parts thereof. Depending on the embodiment, the access panel may or may not be openable or removable by the user who typically wears it.

3. Exemplary Methods of Using the Wearable Health and Treatment Device

The wearable health and treatment device 10 as described with reference to FIGS. 1-3 may be used at least to dispense a treatment substance, such as an ethanol-based hand sanitizer, to detect information regarding a wearer's temperature, and to transmit information regarding the dispensing of a treatment substance and the detected temperature of the wearer. A wearer may use the wearable health and treatment device 10 by first engaging the wearable health and treatment device 10 on his person. Thus, the strap 20 may be configured such that opposite ends thereof comprise clasping means for securing the wearable health and treatment device 10 to the wearer. Examples of clasping means may be magnets, hook-and-loop fasteners, buttons, or the like embedded in the strap 20.

In one exemplary embodiment, the wearable health and treatment device 10 is worn on a wearer's wrist. In this example embodiment, the wearable health and treatment device 10 is worn so that the body temperature capturing component 90 contacts at least a portion of the wearer's skin, e.g., on the palmar side of the wearer's wrist, near to the radius and ulna. Further, the wearable health and treatment device 10 is oriented so that the second cavity 19 defined in the strap 20 is directed toward the wearer's palm. Thus oriented, the wearer then presses or otherwise actuates buttons 22 to dispense a treatment substance into or toward the palm of the wrist on which the wearable health and treatment device 10 is being worn. For example, the wearer may actuate the buttons 22 with the hand opposite the hand on which the wearable health and treatment device 10 is being worn. This allows convenient dispensing of the treatment substance. The wearer may then proceed to apply the treatment substance over both hands to accomplish sanitization.

The wearable health and treatment device 10 may also be used to detect a wearer's temperature. In some embodiments, the wearable health and treatment device 10 is used to detect a wearer's temperature in order to adhere to one or more predetermined protocols. The body temperature capturing component 90 may thus be configured to periodically and/or automatically detect and transmit to the computing device 62 information regarding a wearer's temperature. In various embodiments, the body temperature capturing component 90 periodically and/or automatically detects a wearer's temperature in accordance with an applicable compliance standard. For example, the body temperature capturing component 90 may be configured to detect a wearer's temperature on a repeated basis—say every 60 seconds or so—as dictated by the applicable compliance standard. In these embodiments, the applicable compliance standards may define an allowed (or disallowed) temperature range. In other embodiments, the body temperature capturing component 90 periodically or automatically detects a wearer's temperature in accordance with personal healthcare directives. For example, the body temperature capturing component 90 may be configured to detect a wearer's temperature according to a personal medical diagnosis or regimen so as to monitor a wearer's prognosis. For example, a wearer traveling from a country having a high COVID-19 transmission rate may have a personal medical regimen requiring him to check his temperature twice a day. The body temperature capturing component 90 may therefore be configured to automatically detect the wearer's temperature every 12 hours. In these embodiments, the personal medical diagnosis or regimen may define an allowed (or disallowed) temperature range.

In some other embodiments, detecting a wearer's body temperature may automatically initiate upon engaging or wearing the wearable health and treatment device 10. For example, the body temperature capturing component 90 may be configured to automatically initiate detection of a wearer's body temperature upon contacting the wearer's skin. In these example embodiments, the sensors embedded in the substrate of the body temperature detecting component 90 may be in operable communication with electrical leads, wires or the like housed within the clasping means of the strap 20. The sensors may therefore be configured to detect the respective clasping and un-clasping of the strap 20 that are associated with putting on and removing the wearable health and treatment device 10. In various embodiments, the wearable health and treatment device 10 is further configured to provide an initial sanitation alert upon determination that a wearer has put on the wearable health and treatment device 10. For example, the main display 74 may be configured to indicate such an initial sanitation alert. An initial sanitation alert may be an alert such as a visual, auditory, tactile, or composite alert. In some embodiments, an initial sanitation alert may continue until the buttons 22 are actuated. For example, an initial sanitation alert may be a tactile "buzzing" or other sensation that continues until the buttons 22 are actuated.

In certain embodiments, the body temperature capturing component 90 may be further configured to detect a wearer's body temperature until a termination event occurs. For example, a termination event may be disengaging the wearable health and treatment device 10 from the wearer's person. In such cases when a termination event occurs, the wearable health and treatment device 10 may be configured to transmit a termination alert, i.e., a notification that the wearable health and treatment device 10 has been removed. This embodiment is advantageous in situations such as, for example, those where it is imperative or required that a wearer maintain the wearable health and treatment device 10 on his or her body without interruption, such as in food service.

Moreover, the wearable health and treatment device 10 may be used to detect a wearer's temperature for personal or discrete verification of health. For example, a wearer may desire to verify an acceptable body temperature and sanitize his hands before entering a social environment where social distancing or other protocols are in place due to looming health threats such as e.g., COVID-19. Or, alternatively, the proprietor of an establishment may require such hand sanitization and verification of an acceptable body temperature before entrance. Thus, the body temperature capturing component 90 of some embodiments may be configured to detect a wearer's body temperature on demand. That is, the wearer may satisfy his or her prerogative to detect and display body temperature by engaging the wearable health and treatment device 10 which detects the wearer's body temperature on demand by detecting the clasping of the strap 20 associated with engaging or putting on the wearable health and treatment device.

The wearable health and treatment device 10 may be used to transmit pertinent diagnostic information in order to facilitate compliance with sanitization protocols as well as various other health regimens. Such diagnostic information may be configured to include at least the level or amount of treatment substance remaining in the deformable cartridge 14 and the wearer's body temperature. To that end, the diagnostic information may further include an indication that the level of treatment substance remaining in the deformable cartridge 14 is so low as to warrant discarding the deformable cartridge 14.

It will be understood by those of skill in the art that the above described method of use may also be employed with any of the embodiments illustrated in any of FIGS. 4-8. Modifications during use may be made to incorporate additional or different components described therein, while maintaining the scope of the present disclosure.

4. Exemplary System Comprising the Wearable Health and Treatment Device

Figure 10:
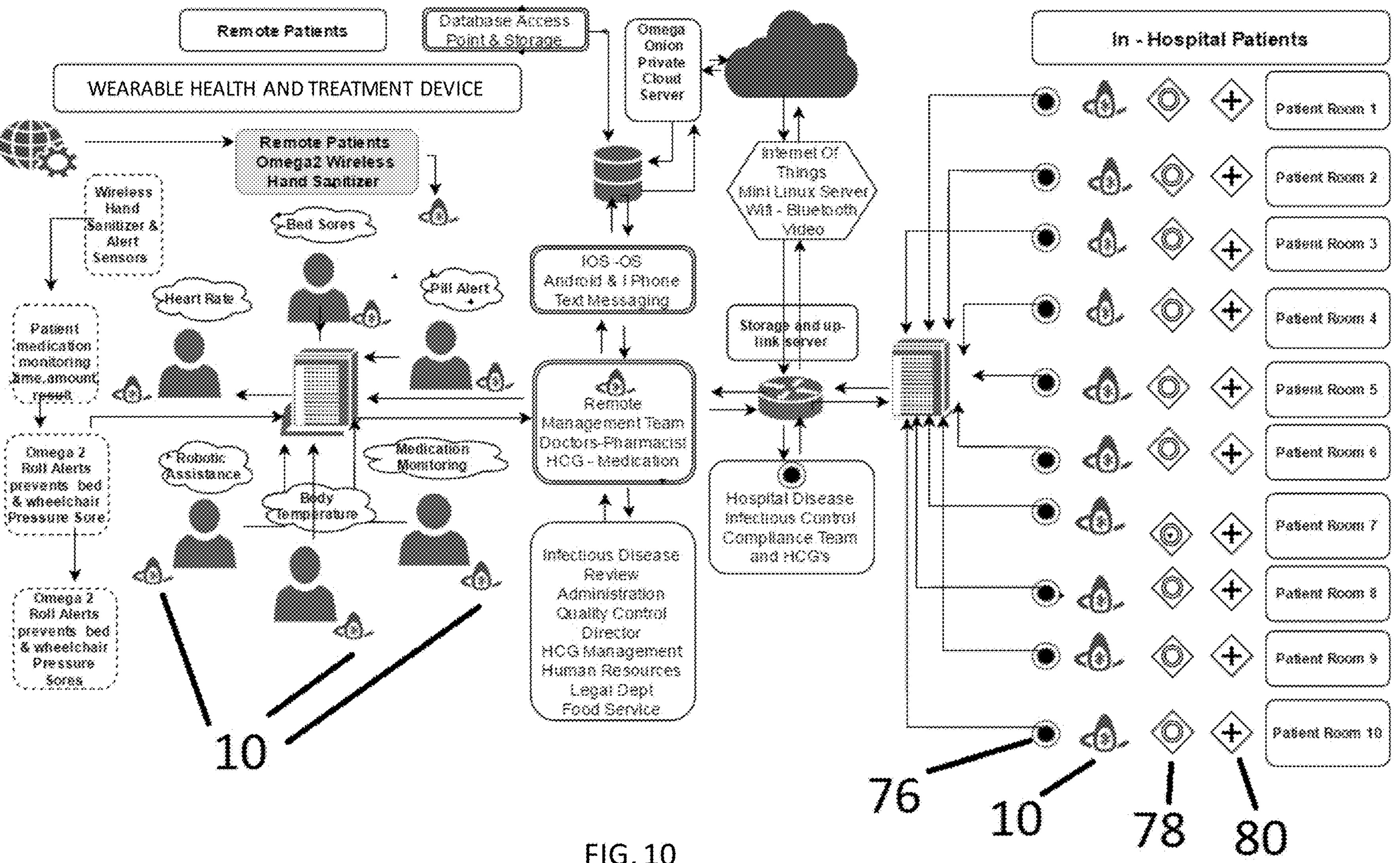
FIG. 10 illustrates a wearable health and treatment device comprising cloud computing according to various embodiments.

FIG. 10 illustrates a wearable health and treatment device 10 comprising cloud computing according to any of the embodiments illustrated in FIGS. 1-8. Particularly, FIG. 10 shows a cloud computing embodiment with servers, including an Onion server, that communicates with computing devices 62 on one or more wearable health and treatment devices 10, through wireless means. A plurality of each computing device 62 is shown, but it is understood by one of skill in the art that one or more of any of the computing devices could be used in a cloud computing embodiment, and one or more servers could be used that are connected to each other through various means. The servers may also be connected to the Internet, enabling further communication with any other device connected to the Internet, as would be understood by one of skill in the art. This is particularly useful for remote patients, e.g., those at home on bed rest.

In a typical application, a group of users in an industry requiring compliance logs of hand sanitization and proof of general health such as the absence of fever (e.g., healthcare, where users would be nurses, doctors, or anyone else with physical patient interaction) would all wear the wearable health and treatment devices 10. Each time sanitizer was dispensed, the computing device 62 would detect the dispensation and wirelessly transmit the dispensation to a compliance log, e.g. through a server such as the Onion Server. Servers may be located on the same floor or in the same facility or may be connected remotely to a facility via the Internet. The compliance episode would be logged, timestamped, and compared with the worker's location and what patient the worker was visiting with at the time. Typically, the computing device 62 would connect wirelessly to other devices though means such as Bluetooth or WiFi, although any wireless communication signal known in the art could be employed, particularly in the healthcare industry where special wireless communication technology may be used because of the presence of machines sensitive to electromagnetic signals.

The plurality of wearable health and treatment devices 10 are shown in the FIG. 10 embodiment as being in wireless communication with a server or servers. Although not shown in this figure, the wearable health and treatment devices 10 could also wirelessly communicate through Bluetooth or WiFi or other wireless means with other computing devices including other wearable health and treatment devices. The wearable health and treatment devices 10 may also have one-way RFID communication. Typically, however, the wearable health and treatment devices 10 would only communicate with a server or plurality of servers. Such communication could be accomplished through an access point 76, e.g., a router or wireless access point, which would be located e.g., in patient rooms and throughout the hospital to ensure uninterrupted communication between the computing device and server(s).

In one cloud-computing embodiment, the wearable health and treatment device 10 would constantly transmit the level or amount of sanitizer remaining in a healthcare worker's cartridge 14 to a server where other software could manipulate, transmit, alert, or display the information. For example, an alert could be displayed on a manager's computer dashboard showing that a worker was low on sanitizer solution. When the treatment substance in a healthcare worker's cartridge is completely expired, the worker would remove and replace the expired cartridge with a new cartridge of the same or a different treatment substance. FIG. 10 shows one or more compliance sensors 78 that may be located in various places in a healthcare or other facility. In this embodiment, compliance sensors 78 are placed in connection with the patient rooms, but it is understood that typically they would be throughout the hospital. In a typical application, the plurality of sensors 78 would be located near a door used by a healthcare provider to access a patient, e.g., in a waiting room, examination room, or operating room. More broadly, such sensors would be placed at any entrance or exit nodes flagged by appropriate compliance employees where hand hygiene and sanitation compliance is important or critical. The compliance sensor 78 would detect whether a healthcare provider entered or exited via wireless communication technology, most typically Bluetooth or RFID, and would notify a server or servers. The server in communication with the wearable health and treatment device 10 would then track whether the user actuated the wearable health and treatment device 10 to apply a treatment substance (e.g., sanitizer) within a certain period of time customizable by an employer or compliance manager or whether a wearer's temperature fell outside an allowed temperature range. The server could send any information or communications to the wearable health and treatment device 10 causing any of the indicators 66, 68, 70, 72 or the main display 74 to change status or issue a warning or notice of hand hygiene non-compliance and unacceptable body temperature to the user. Similarly, tracking sensors on wall sanitizer dispensers or sinks 80 could sense when a device on a user's wrist is nearby, and could determine whether sanitizer is dispensed, or whether hot water and soap are used, indicating that hand hygiene compliance has been achieved. This information would be communicated back to a server, and various information could be communicated to the device. Handwashing sensors would operate in a similar fashion to the tracking sensors on wall sanitizer dispensers 80 and could detect the proximity of a wearer's wearable health and treatment device 10, whether the faucet has been activated, for how long, the temperature of the water released, and the type and amount of soap or handwashing substance released.

In other embodiments, compliance sensors 78 could send and/or receive communication from the computing device 62 and could be affixed near or on entryways or wall sanitizers where compliance is necessary to determine if anyone who is entering has recently sanitized their hands or been detected to have a body temperature outside an allowed temperature range. For example, the door to a surgical operating room might have such a device affixed to the door or near it. If anyone attempted to enter with a fever or without having sanitized their hands within a certain period of time then an alarm (e.g., buzzing, or sounds either in the room or facility or on the wearable dispenser) could notify the person and others nearby who was not in compliance, and/or would notify other healthcare workers or management responsible for maintaining patient safety, sanitization compliance, or employee compliance in real-time.

All health and treatment events, whether detection of fever, compliant dispensations of sanitizer, or hand washing, or non-compliance for failure to actuate/sanitize within in an actuation compliance time (for whatever the reason) may be communicated to and tracked by a server. The server, in turn, could be accessed by, or could push alerts, notifications or other information to employees or managers (such as a team leader, floor nurse manager, or hand hygiene compliance manager) on handheld devices such as pagers or smartphones, or to desktop workstations. In the foodservice industry, alerts may be especially important and could be sent in real time to a restaurant manager if wait-staff are in non-compliance (e.g., sensors and wearable devices as described herein could detect wait-staff exiting a bathroom and failing to sanitize or wash hands or arriving to work with fever). The cloud computing system is operable with, and may communicate with PC, Android, OS, iOS and other operating systems.

Compliance databases and logs store information about a wearer's body temperature, the compliance location, time, the user(s), and what substance was dispensed. Other information could also be logged or stored to promote efficiency such as tracking the amount of sanitizer remaining in wall-based sanitizer stations 80 or in cartridges 14 and the amount of time taken for proper handwashing. Hardware add-ons or additional sensors connected to an Omega2 computing device could track users throughout the facility or hospital in real time, and this data could be gathered, stored, and analyzed.

Typically, a user such as a nurse or healthcare practitioner is assigned to one wearable health and treatment device 10. Assignment is typically either by a login process on the computing device 62, including via touch-ID, or via a unique code or marker in the computing device 62 that may be communicated to a server. Because each individual can typically be recognized by his or her wearable device, this allows the server to provide notifications or a notification nudge to help ensure compliance. A notification nudge ("nudge") is a type of alert that the server will send to the user's uniquely identifiable wearable device via a visual or audible alert on the device through indicators 66, 68, 70, 72, or the main display 74, or another human interface. A nudge is communicated when and if the user needs to take an action. For example, compliance sensors 78 may prompt a user, through the server, or even directly to the wearable health and treatment device 10, to comply with hand hygiene within an actuation compliance time. Even though signs may be posted, or the user may have training to sanitizer his or her hands after entering or exiting a certain area, workflow pattern fatigue may set in after time and the user may forget. The "nudge" feature helps to prevent this. It is noted for clarification that while "wearer" is typically used as someone who is wearing the wearable health and treatment device 10, a "user" in the cloud computing context is actually any person authorized or otherwise accessing the network of which the wearable health and treatment devices 10 are a part. This can include, e.g., compliance officers, agents, or managers, or healthcare providers monitoring information on the network.

While nudges are typically embodied in the hand hygiene context or in the context of dispensing the treatment substance in the wearable device, they may also be used to alert and monitor bed rolling (for example through an accelerometer in the computing device 62) and wheelchair movement to prevent bed sores, and to prompt users to take medication. Nudges may be pre-programmed into the wearable health and treatment device 10 or may be pushed by a server via an algorithm or monitored by a compliance agent. Nudges may also be pushed by other devices such as desktop computers, smartphones, or servers, through a server and to the wearable health and treatment device 10. The nudges may also provide information through the indicators 66-72, or on the main display 74. Such information could include instructions, details about risks, warnings, and may show which pill a user should take, the color of the pill, and the time it should be taken. Multiple nudges may be pushed or pre-programmed to ensure compliance. Nudges may be used for inpatients or remote patients. In particular, when nudges are used in connection with remote patients, they have the effect of reducing readmissions. Nudges, however, are only one type of alert.

5. Conclusion

It is emphasized that the embodiments described above are merely examples of the disclosed systems, methods, and means. Many variations and modifications are understood to be able to be made to the embodiments described above, and those variations and modifications are to be included within the scope of this disclosure and invention.

That which is claimed:

1. A wearable device comprising:

a wearable strap, the wearable strap having a first cavity extending along a portion of the wearable strap;

a deformable cartridge defining a distal substrate of the wearable strap, the deformable cartridge positioned substantially within the first cavity and configured to contain and selectively dispense a treatment substance;

a body temperature capturing component defining a proximate substrate of the wearable strap, an inner surface of the body temperature capturing component being in contact with a portion of a wearer's skin, and an outer surface of the body temperature capturing component being disposed adjacent an inner surface of the deformable cartridge;

a set of buttons embedded in a portion of the wearable strap spaced away from the first cavity, the set of buttons being configured to initiate dispensing of the treatment substance from the deformable cartridge when actuated; and a removable encasing portion having a curvature corresponding with a curvature of the strap, the removable encasing portion being configured to removably engage the first cavity defined by the strap and encase the deformable cartridge and the body temperature capturing component therein.

2. The wearable device of claim 1, wherein the body temperature capturing component comprises a flexible substrate having sensing elements embedded therein.

3. The wearable device of claim 2, wherein the sensing elements are embedded in the flexible substrate at a concentration of 1 per cm2, 2 per cm2, or 5 per cm2.

4. The wearable device of claim 2, wherein the body temperature capturing component comprises a temperature sensing portion having a size corresponding with a size of an opening of the first cavity defined by the strap.

5. The wearable device of claim 1, wherein the strap comprises a material that is resistant to microbe growth.

6. The wearable device of claim 1, wherein the removable encasing portion comprises a material that is resistant to microbe growth.

7. A wearable sanitizing system comprising:

a wearable strap, the wearable strap having a first cavity extending along a portion of the wearable strap;

a deformable cartridge defining a distal substrate of the wearable strap, the deformable cartridge positioned substantially within the first cavity and configured to contain and selectively dispense a treatment substance;

a body temperature capturing component defining a proximate substrate of the wearable strap, an inner surface of the body temperature capturing component being in contact with a portion of a wearer's skin, and an outer surface of the body temperature capturing component being disposed adjacent an inner surface of the deformable cartridge;

a set of buttons embedded in a portion of the wearable strap spaced away from the first cavity, the set of buttons being configured to initiate dispensing of the treatment substance from the deformable cartridge when actuated;

a removable encasing portion having a curvature corresponding with a curvature of the strap, the removable encasing portion being configured to removably engage the first cavity defined by the strap and encase the deformable cartridge and the body temperature capturing component therein; and a processor embedded in the wearable strap, the processor configured in operable communication with the body temperature capturing component and the deformable cartridge for receiving data from the body temperature capturing component and the deformable cartridge, and for transmitting the received data over a network to a distributed computing device remotely located relative to the wearable strap.

8. The system of claim 7, wherein the wearable strap further comprises a display configured to indicate diagnostic information including at least an amount of the treatment substance contained within the deformable cartridge, and a body temperature of a wearer.

9. The system of claim 8, wherein the diagnostic information indicates that the deformable cartridge may be discarded.

10. The system of claim 8, wherein the diagnostic information further includes an allowed temperature indicator, chosen from the group consisting of a visual indicator, an audible indicator, a tactile indicator, and a composite indicator that indicates that the body temperature of the wearer is within an allowed temperature range.

11. The system of claim 8, wherein the diagnostic information further includes a disallowed temperature indicator, chosen from the group consisting of a visual indicator, an audible indicator, a tactile indicator, and a composite indicator that indicates that the body temperature of the wearer is not within an allowed temperature range.

* * * * *